US009675264B2

United States Patent
Acquista et al.

(10) Patent No.: US 9,675,264 B2
(45) Date of Patent: Jun. 13, 2017

(54) SYSTEM AND METHOD FOR MONITORING AND DIAGNOSING PATIENT CONDITION BASED ON WIRELESS SENSOR MONITORING DATA

(71) Applicant: Peerbridge Health, Inc., New York, NY (US)

(72) Inventors: Angelo Joseph Acquista, New York, NY (US); Avi Kometz, East Quogue, NY (US); Leung-Hang Ma, Brooklyn, NY (US); John Shambroom, Framingham, MA (US)

(73) Assignee: Peerbridge Health, Inc., New York, NY (US)

( * ) Notice: Subject to any disclaimer, the term of this patent is extended or adjusted under 35 U.S.C. 154(b) by 453 days.

(21) Appl. No.: 14/216,174

(22) Filed: Mar. 17, 2014

(65) Prior Publication Data

US 2014/0275928 A1   Sep. 18, 2014

Related U.S. Application Data

(60) Provisional application No. 61/787,772, filed on Mar. 15, 2013, provisional application No. 61/924,986, filed on Jan. 8, 2014.

(51) Int. Cl.
*A61N 1/365* (2006.01)
*A61B 5/0408* (2006.01)
(Continued)

(52) U.S. Cl.
CPC .......... *A61B 5/04085* (2013.01); *A61B 5/046* (2013.01); *A61B 5/04028* (2013.01);
(Continued)

(58) Field of Classification Search
CPC ............ A61N 1/36128; A61N 1/36132; A61N 1/36135; A61N 1/362; A61N 1/3621;
(Continued)

(56) References Cited

U.S. PATENT DOCUMENTS 2,714,380 A   8/1955   Freshman
4,082,086 A   4/1978   Page et al.
(Continued)

FOREIGN PATENT DOCUMENTS

WO   0122876 A1   4/2001
WO   02/41772 A1   5/2002
(Continued)

OTHER PUBLICATIONS

Office Action issued on Nov. 16, 2015 in U.S. Appl. No. 14/699,566.
(Continued)

*Primary Examiner* — Allen Porter, Jr.
(74) *Attorney, Agent, or Firm* — Stroock & Stroock & Lavan LLP

(57) ABSTRACT

A device adapted to attach to a subject for detecting an ECG signal of the subject. The device includes a first, a second, and a third electrode, where the electrodes form an orthogonal configuration. Two channels of ECG data can be obtained using a common electrode, and can be further combined to obtain a further channel using vector mathematics. The channel combination can be performed at vector angles suitable for optimizing the detection of various features of the ECG spectra of the subject. A method of using an implantable cardiac device together with surface-attached wireless sensor(s) is also provided where the acquired data from the implantable cardiac device and from the surface-attached wireless sensor(s) are both used for diagnosing patient's heart conditions and administering appropriate therapies.

7 Claims, 10 Drawing Sheets

(51) Int. Cl.
*A61N 1/39* (2006.01)
*G06F 19/00* (2011.01)
*A61B 5/0402* (2006.01)
*A61B 5/0456* (2006.01)
*A61B 5/046* (2006.01)
*A61B 5/00* (2006.01)
*A61B 5/04* (2006.01)
*A61B 5/0452* (2006.01)
*A61B 5/0464* (2006.01)

(52) U.S. Cl.
CPC .......... *A61B 5/0456* (2013.01); *A61B 5/6823* (2013.01); *A61N 1/365* (2013.01); *A61N 1/36585* (2013.01); *A61N 1/3956* (2013.01); *A61N 1/3987* (2013.01); *G06F 19/345* (2013.01); *A61B 5/0006* (2013.01); *A61B 5/04011* (2013.01); *A61B 5/0452* (2013.01); *A61B 5/0464* (2013.01); *A61B 5/4848* (2013.01); *A61B 5/6832* (2013.01); *A61B 5/746* (2013.01); *A61B 2560/0412* (2013.01); *A61B 2562/04* (2013.01); *A61B 2562/164* (2013.01)

(58) Field of Classification Search
CPC .... A61N 1/3622; A61N 1/3624; A61N 1/365; A61N 1/36507; A61N 1/36585; A61N 1/36592; A61N 1/3702; A61N 1/37252; A61N 1/37282; A61N 1/37288
See application file for complete search history.

(56) References Cited

U.S. PATENT DOCUMENTS

| | | | |
|---|---|---|---|
| 4,136,690 | A | 1/1979 | Anderson et al. |
| 4,308,870 | A | 1/1982 | Arkans |
| 4,622,979 | A | 11/1986 | Katchis et al. |
| 4,938,228 | A | 7/1990 | Righter et al. |
| 5,191,891 | A | 3/1993 | Righter |
| 5,226,425 | A | 7/1993 | Righter |
| 5,365,935 | A | 11/1994 | Righter et al. |
| 5,544,661 | A | 8/1996 | Davis et al. |
| 5,568,814 | A | 10/1996 | Gallant et al. |
| 5,581,369 | A | 12/1996 | Righter et al. |
| 5,730,143 | A | 3/1998 | Schwarzberg |
| 5,931,791 | A | 8/1999 | Saltzstein et al. |
| 5,941,829 | A | 8/1999 | Saltzstein et al. |
| 6,223,073 | B1 | 4/2001 | Seegobin |
| 6,470,893 | B1 | 10/2002 | Boesen |
| 6,505,067 | B1 | 1/2003 | Lee et al. |
| 6,716,165 | B1 | 4/2004 | Flanders et al. |
| 6,754,523 | B2 | 6/2004 | Toole |
| 6,778,851 | B2 | 8/2004 | Anderson |
| 6,871,089 | B2 | 3/2005 | Korzinov et al. |
| 6,897,788 | B2 | 5/2005 | Khair et al. |
| 6,970,737 | B1 | 11/2005 | Brodnick et al. |
| 7,142,907 | B2 | 11/2006 | Xue et al. |
| 7,161,484 | B2 | 1/2007 | Tsoukalis |
| 7,171,166 | B2 | 1/2007 | Ng et al. |
| 7,194,298 | B2 | 3/2007 | Massicotte et al. |
| 7,194,299 | B2 | 3/2007 | Shvilkin et al. |
| 7,206,630 | B1 | 4/2007 | Tarler |
| 7,266,408 | B2 | 9/2007 | Bojovic et al. |
| 7,272,428 | B2 | 9/2007 | Hopman et al. |
| 7,289,844 | B2 | 10/2007 | Misczynski et al. |
| 7,382,247 | B2 | 6/2008 | Welch et al. |
| 7,412,282 | B2 | 8/2008 | Houben |
| 7,647,093 | B2 | 1/2010 | Bojovic et al. |
| 7,840,259 | B2 | 11/2010 | Xue et al. |
| 7,904,133 | B2 | 3/2011 | Gehman et al. |
| 7,996,073 | B2 | 8/2011 | Busche et al. |
| 8,046,059 | B2 | 10/2011 | Cho et al. |
| 8,180,440 | B2 | 5/2012 | McCombie et al. |
| 8,209,002 | B2 | 6/2012 | Vajdic et al. |
| 8,255,041 | B2 | 8/2012 | Istvan et al. |
| 8,290,574 | B2 | 10/2012 | Feild et al. |
| 8,301,236 | B2 | 10/2012 | Baumann et al. |
| 8,315,695 | B2 | 11/2012 | Sebelius et al. |
| 8,352,018 | B2 | 1/2013 | Xue et al. |
| 8,433,399 | B1 | 4/2013 | Nosrati et al. |
| 8,473,039 | B2 | 6/2013 | Michelson et al. |
| 8,515,531 | B2 | 8/2013 | Costa Ribalta et al. |
| 8,538,510 | B2 | 9/2013 | Toledo et al. |
| 8,588,894 | B2 | 11/2013 | Saba et al. |
| 8,613,709 | B2 | 12/2013 | Bishay et al. |
| 8,620,415 | B2 | 12/2013 | Shani et al. |
| 8,639,319 | B2 | 1/2014 | Hugh et al. |
| 9,101,264 | B2 | 8/2015 | Acquista |
| 2002/0035334 | A1 | 3/2002 | Meij et al. |
| 2002/0045836 | A1 | 4/2002 | Alkawwas |
| 2003/0088289 | A1* | 5/2003 | Levine ............... A61N 1/37 607/30 |
| 2004/0039254 | A1 | 2/2004 | Stivoric et al. |
| 2005/0140964 | A1 | 6/2005 | Eschenauer et al. |
| 2005/0288600 | A1 | 12/2005 | Zhang et al. |
| 2006/0235322 | A1 | 10/2006 | Simske et al. |
| 2007/0239220 | A1 | 10/2007 | Greenhut et al. |
| 2007/0279217 | A1 | 12/2007 | Venkatraman et al. |
| 2008/0009694 | A1 | 1/2008 | Hopman et al. |
| 2008/0129465 | A1 | 6/2008 | Rao |
| 2008/0281180 | A1 | 11/2008 | Choe et al. |
| 2009/0167531 | A1 | 7/2009 | Ferguson |
| 2009/0171227 | A1 | 7/2009 | Dziubinski et al. |
| 2010/0081946 | A1 | 4/2010 | Garudadri et al. |
| 2010/0249541 | A1 | 9/2010 | Geva et al. |
| 2011/0077497 | A1 | 3/2011 | Oster et al. |
| 2011/0213216 | A1 | 9/2011 | McKenna et al. |
| 2011/0221595 | A1 | 9/2011 | Koraichi et al. |
| 2011/0270069 | A1 | 11/2011 | Acquista |
| 2012/0330171 | A1 | 12/2012 | Zhang et al. |
| 2013/0060156 | A1 | 3/2013 | Gregg et al. |
| 2013/0116533 | A1 | 5/2013 | Lian et al. |
| 2015/0313505 | A1 | 11/2015 | Acquista |

FOREIGN PATENT DOCUMENTS

| | | |
|---|---|---|
| WO | 2006/045793 A1 | 5/2006 |
| WO | 2008064682 A2 | 6/2008 |
| WO | 2008064682 A3 | 6/2008 |
| WO | 2009/132826 A1 | 11/2009 |
| WO | 2013128364 A1 | 9/2013 |

OTHER PUBLICATIONS

Office Action issued on Dec. 2, 2015 in U.S. Appl. No. 14/215,965.
Examination Report issued on Feb. 4, 2015 in European Patent Application No. 07796145.6.
International Search Report and Written Opinion issued on Aug. 27, 2014 in International Application No. PCT/US2014/030501.
Extended European Search Report issued on Nov. 7, 2016 in European Patent Application No. 14763795.3.
Examination Report issued on Nov. 1, 2016 in Saudi Arabian Patent Application No. 515361177.

* cited by examiner

SYSTEM AND METHOD FOR MONITORING AND DIAGNOSING PATIENT CONDITION BASED ON WIRELESS SENSOR MONITORING DATA

CROSS-REFERENCE TO RELATED APPLICATIONS

This application claims priority to U.S. provisional application No. 61/787,772, filed on Mar. 15, 2013, and U.S. provisional application No. 61/924,986, filed Jan. 8, 2014, the disclosure of each of which is incorporated herein by reference in its entirety.

FIELD OF THE INVENTION

The present invention relates to one or more wireless sensors, and a network of wireless sensors, for monitoring, in real time (or quasi real time), a patient's vital signs, such as various hemodynamic parameters of the patient. In addition, the present invention relates to using wireless surface-attached sensors with implantable heart monitoring devices for providing improved diagnosis, monitoring, and treatment of medical conditions. Further, the present invention relates to integration of such wireless sensors with an electronic medical record storage and management system for managing patient healthcare, such as providing clinical decision support, facilitating diagnosis and validating treatment options.

BACKGROUND

Monitoring various vital signs of a patient has been an important aspect of hospital patient care, especially for patients with diseases at advanced stages, suffering from severe trauma, or in other emergency settings. Additionally, outpatient monitoring of various physiological conditions are being increasingly used for evaluation of patient health conditions as well as early detection and treatment of heart diseases, diabetes, and other diseases. For example, an electrocardiogram (ECG or EKG) can be used to evaluate the heart condition of a patient, where electrodes are placed at certain locations on the chest, arms, and/or legs. These electrodes can be connected to an ECG machine by lead wires, and the electric signals received by the ECG machine can be analyzed and displayed for the physician's information and further interpretation.

Attempts have also been made to develop systems to improve a patient's comfort, freedom and privacy by decreasing the number and volume of devices directly or indirectly attached to the patient. For example, U.S. Pat. No. 7,979,111 discloses a wireless electrode arrangement and method for patient monitoring, where a plurality of wireless electrodes suitable for attachment to the surface of the body of a patient are capable of continuously monitoring of a subject wirelessly. Copending U.S. patent application Ser. No. 13/835,049 (published as U.S. Patent Application Publication No. 20130204100) further describes a network of wireless sensors for monitoring hemodynamic parameters of a subject. The disclosures of both of these documents are incorporated in its entirety by reference herein.

Implantable devices such as implantable cardioverter defibrillators (ICDs) or pacemakers are often indicated for patients who have or are at increased risk for various heart conditions related to the heart's electrical system, such as ventricular and atrial arrhythmias including but not limited to ventricular fibrillation, ventricular tachycardia, atrial fibrillation, and bradycardia, etc. These implantable devices can monitor and/or manage certain heart conditions of the patients and prevent or control heart episodes that would otherwise interfere with daily life or be life threatening, and can therefore allow patients with certain heart conditions to carry on their normal lives with relatively few restrictions and generally low level of discomfort.

However, there can be limiting factors for these implantable devices such as inaccuracy in detecting the relevant heart condition episodes and administering appropriate therapies. For example, the positioning and contact of the leads of the ICDs with the heart muscle can be affected by the patient's movement, and the problem is more acute for young and more active patients. ICDs can also have lead failures after being worn by a patient for an extended period of time, e.g., a number of years. Lead positioning errors and failures can cause inaccurate or distorted electrograms, and thereby may lead to insufficient, overly aggressive, or otherwise inappropriate cardiac intervention, such as excessive number of unwarranted shocks or shocks with unnecessarily large magnitude, which can cause discomfort, pain, and other undesirable effects on the quality of life of the patients.

Since the last decade, and especially after the enactment of the American Recovery and Reinvestment Act of 2009, healthcare providers are facing more regulations regarding electronic record management (EMR) and electronic health records (EHR) (or personal health record (PHR)). Meanwhile, medical software providers have been developing a plethora of systems that facilitate electronic data storage and management to enable healthcare providers to be in compliance with such increased regulations. For example, a patient's EHR can provide a longitudinal electronic record of patient health information gathered during one or more encounters in a care delivery setting, which can include information such as patient demographics, medications, vital signs, medical history, laboratory test results, and radiology reports, etc. The EHR can also be used to provide decision support, quality management, and outcomes reporting.

There is a need for a system that integrates the real time monitoring capability of wireless sensors worn by a patient with the data storage and processing capabilities afforded by electronic health records management systems for personalized monitoring and clinical decision support, improving accuracy in diagnosis and validating treatment options proposed by physicians.

SUMMARY OF THE INVENTION

According to some embodiments of the present invention, a system for monitoring a subject is provided. The system includes a plurality of wireless sensors attachable to or implantable in the subject, each sensor comprising a sensing component configured to detect a signal corresponding to at least one hemodynamic condition of the subject, and a communication component configured to wirelessly transmit the detected signal to another of the plurality of wireless sensors. The system further comprises a monitoring device configured to receive signals from at least one of the plurality of wireless sensors. At least one of the plurality of wireless sensors is selected to be a control node, the control node further configured to wirelessly receive detected signals from another of the plurality of wireless sensors, and to wirelessly relay the received signals to the monitoring unit.

In some embodiments of the system, the plurality of wireless sensors are configured to form a mesh network.

In some embodiments of the system, the vital signs include hemodynamic parameters selected from one or more of pulse oximetry, oxygen saturation, oxyhemoglobin saturation, blood glucose level, blood pressure, blood velocity, blood flow rate, respiratory rate, pulse rate, $CO_2$ level, drug concentration, blood protein concentration, blood alcohol level, heart rate, heart rhythm, heart rate variability, organic or inorganic substance concentration, cardiac activity, cardiac output, pH levels, pathogens and galvanic skin response.

In some embodiments of the system, at least one of the plurality of wireless sensors of the system includes a sensing component configured to detect a signal corresponding to a first hemodynamic parameter of the subject, and at least another of the plurality of wireless sensors includes a sensing component configured to detect a signal corresponding to a second hemodynamic parameter of the subject, the second hemodynamic parameter being different from the first hemodynamic parameter.

In some embodiments of the system, at least one of the plurality of sensors is implantable.

In some embodiments of the system, at least one of the plurality of sensors is configured to be attachable to the skin of a patient.

In some embodiments of the system, the sensing component includes at least one of an electromagnetic detector, a thermal detector, a pressure detector, an ultrasonic detector, an optical detector and a chemical detector, a magnetic detector, a laser detector, and an x-ray detector.

In some embodiments of the system, the monitoring device is a portable computing device.

In some embodiments of the system, at least one of the plurality of wireless sensors is a surface-attachable ECG sensor comprising three electrodes arranged in an orthogonal configuration.

In some embodiments, the system includes an accelerometer and/or a gyrometer (or gyroscope) for determining a patient's movement, detecting the patient's activity level (e.g., paces and distance traveled by a patient, calories burned, etc.) and/or events that relate to a fall or an accident that may warrant immediate medical attention. In certain embodiments, the system also include a GPS receiver or other positioning devices to determine the geographical location of the patient.

According to some embodiments of the present invention, a method of managing a heart condition for a subject is provided. The method includes: (a) detecting intrathoracic electrogram signals of the subject over a first defined period of time by at least one implantable cardiac device having a sensor component implanted in the heart of the subject; (b) determining whether the subject is experiencing a heart condition based on the electrogram signals; (c) detecting ECG signals of the subject over the first defined period of time by at least one surface sensor attached to the skin of a subject; (d) based upon the detected ECG signals in step (c), determining parameters of an action of a therapy to be performed by the at least one implantable device, the action being capable of influencing the electrical system of the heart of the subject in order to address the heart condition; and (e) performing, by the implantable cardiac device, the action with the determined parameters in step (d).

In some embodiments of the method, the heart condition includes one or more of ventricular fibrillation, ventricular tachycardia, atrial fibrillation, and bradycardia.

In some embodiments of the method, the at least one implantable cardiac device is a pacemaker.

In some embodiments of the method, the action to be performed is pacing the heart with electric current, and the parameters of the action include at least one of the magnitude of the pacing current and the timing of administering of the pacing current.

According to some embodiments of the present invention, a method of monitoring a condition for a subject is provided, which includes: (a) detecting signals relevant to one or more vital signs of a subject by one or more wireless sensors attached to the skin or implanted in the body of the subject; (b) wirelessly receiving, by a computing device, the signals from the one or more wireless sensors; (c) accessing, by the computing device, at least one medical record of the subject; and (d) using a processor of the computing device to make a diagnosis regarding a condition of the subject based on the signals received from the wireless sensors and the accessed medical record. In certain embodiments of the method, the signals are live signals acquired by the one or more wireless sensors in real time. In certain embodiments, the medical record is retrieved from a database containing the subject's EMR. In certain embodiments, the database is updated by including the diagnosis in the subject's EMR.

According to some embodiments of the present invention, a method of monitoring a condition for a subject is provided, which includes: (a) detecting signals relevant to one or more vital signs of a subject by one or more wireless sensors attached to the skin or implanted in the body of the subject; (b) wirelessly receiving, by a computing device, the signals from the one or more wireless sensors; (c) making a diagnosis utilizing a processor of the computing device regarding a condition of the subject based on the signals received from the wireless sensors; (d) accessing, by the computing device, at least one medical record of the subject; and (e) determining, by the computing device, a health status of the subject based on the diagnosis made in step (c) and the medical record accessed in step (d). In certain embodiments, the method further comprises updating a parameter in a treatment being applied to the patient according to the health status of the patient as determined in (e). In certain embodiments, the method further comprises sending a notification to one or more predetermined caregivers or medical personnel according to the health status of the patient as determined in (e). In other embodiments, the method further comprises modifying a setting under which the wireless sensors acquire the signals according to the health status of the patient as determined in (e). In certain embodiments, the medical record is retrieved from a database containing the subject's EMR, and the method further comprises updating the database to include the health status in the subject's EMR. In other embodiments, the health status relates to whether the subject is in compliance with a prescribed therapy.

According to some embodiments of the present invention, a device adapted to attach to a subject for detecting an ECG signal of the subject is provided. The device includes a first electrode, a second electrode, and a third electrode, each of the electrodes having an end for contacting an area of the skin of the subject. The directional positioning from the end of the second electrode to the end of the first electrode is substantially perpendicular to the directional positioning from the end of the third electrode to the end of the first electrode. Each of the electrodes are electrically connected to a circuit configured to obtain two channels of ECG data, the first channel measuring a difference in electric signals between the first electrode and the second electrode, and the second channel between the first electrode and the third electrode.

In some embodiments, the device further comprises a communication component configured to wirelessly transmit the signals measured by the circuit to an external computing device. In some embodiments, the first, second and third electrodes of the device are each positioned near a distal end of a star-shaped substrate. In certain embodiments, the device is further configured to combine the two channels of ECG data into a third channel using vector mathematics.

According to some embodiments of the present invention, a method of operating the above-described device is provided, which includes: acquiring a first channel and a second channel of ECG data using the first, the second, and the third electrodes; and combining the first and second channels of ECG data into a third channel using vector mathematics. In some embodiments of the method, the combining is performed by combining the first channel and the second channel at a vector angle that maximize the chance of detecting atrial fibrillation. In some embodiments, the combining is performed by combining the first channel and the second channel at a vector angle that maximizes the magnitude of a P wave, if existent, in the third channel. In other embodiments, the combining is performed by combining the first channel and the second channel at a vector angle that maximizes the magnitude of a R wave. In yet other embodiments, the combining is performed by combining the first channel and the second channel at a vector angle that maximizes the changes in S-T segment from heartbeat to heartbeat.

According to some embodiments of the present invention, a method of managing a heart condition for a subject is provided. The method includes (a) detecting intrathoracic electrogram signals of the subject over a first defined period of time by at least one implantable cardiac device having a sensor component implanted in the heart of the subject; (b) determining whether the subject is experiencing a heart condition based on the electrogram signals; (c) detecting ECG signals of the subject over the first defined period of time by at least one surface sensor attached to the skin of a subject; (d) determining whether the subject is experiencing the heart condition based on the ECG signals; (e) based upon the results of each of steps (b) and (d), determining whether to perform an action by the implantable cardiac device of a therapy to influence the electrical system of the heart of the subject in order to address the heart condition; and (f) performing, by the implantable cardiac device, the action if the determination result in (e) is positive.

In some embodiments of the method, the at least one implantable cardiac device is an implantable cardioverter defibrillator or a pacemaker. In some embodiments, the heart condition includes one or more of ventricular fibrillation, ventricular tachycardia, atrial fibrillation, and bradycardia. In certain embodiments, the determining in (e) further comprises: when the result of (b) is negative, determining not to perform the action.

In other embodiments of the method, the determining in (c) further comprises: when the results of (b) and (d) are both positive, determining to perform the action.

In further embodiments, the method further includes: when the result of (b) is positive and the result of (d) is negative, (g) repeating (a)-(d) for a predetermined number of times; and (j) determining whether to perform the action of the therapy based on the combination of determination result of each of the repetitions in (g).

In some embodiments, the surface sensor includes a communication component configured to wirelessly transmit the ECG signals detected in (a) to the implantable cardiac device, and wherein the determination in each of (b), (d), and (e) is performed by a processor of the implantable cardiac device.

In some embodiments, the method further includes: (g) wirelessly sending, by the at least one implantable cardiac device, selected information relating to at least one of the electrogram signals in (a), the determination result in (b), and the determination result in (e), to the at least one surface sensor; and (h) wirelessly sending, by the at least one surface sensor, the information received from the at least one implantable cardiac device, as well as selected information relating to at least one of the ECG signals in (c) and the determination result in (d), to an external computing device for storage or further analysis. In further embodiments, the method includes sending an alert to a medical personnel based on the information received by the computing device.

In some embodiments, the determination in each of (b), (d), and (e) is performed by a computing device wirelessly linked to each of the at least one surface sensor and the at least one implantable cardiac device based on the ECG signals and electrogram signals received by the computing device from the at least one surface sensor and the at least one implantable cardiac device.

BRIEF DESCRIPTION OF THE DRAWINGS

The various aspects and embodiments disclosed herein will be better understood when read in conjunction with the appended drawings, wherein like reference numerals refer to like components. For the purposes of illustrating aspects of the present application, there are shown in the drawings certain preferred embodiments. It should be understood, however, that the application is not limited to the precise arrangement, structures, features, embodiments, aspects, and devices shown, and the arrangements, structures, features, embodiments, aspects and devices shown may be used singularly or in combination with other arrangements, structures, features, embodiments, aspects and devices. The drawings are not necessarily drawn to scale and are not in any way intended to limit the scope of this invention, but are merely presented to clarify illustrated embodiments of the invention. In these drawings.

DETAILED DESCRIPTION

Figure 1:
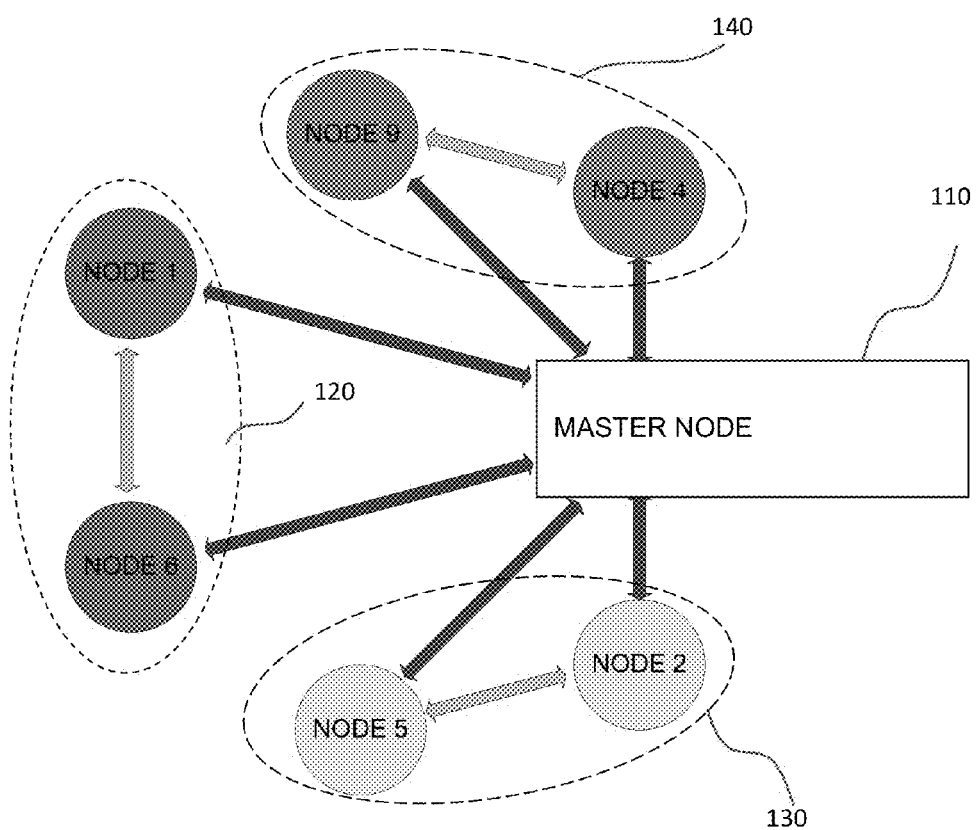
FIG. 1 is a schematic block diagram of a network structure including a plurality of wireless sensors and a master node and communication modes therebetween in accordance with one embodiment of the present invention.

Certain embodiments of the present invention will now be discussed with reference to the aforementioned figures. In one embodiment, the present invention provides a system for managing healthcare for a subject (which used interchangeably herein with a "patient"). The system includes a plurality of wireless sensors suitable for attachment to the skin of a subject or implantable in the body of the subject. The plurality of wireless sensors can form a network. The type of network may utilize a routing topology include: star, mesh, pseudo-mesh network, or any other routing topology. Each of the sensors can include a sensing component configured to detect a signal corresponding to at least one physiological condition of the subject, and a communication component configured to wirelessly transmit the detected signal to either another wireless sensor or an external monitoring unit. The communication component of selected sensors can also be configured to receive and/or relay signals transmitted from other wireless sensors.

As described herein, a wireless sensor includes a sensing component configured to detect a signal corresponding to a physiological condition, such as vital signs including hemodynamic parameters of a patient. Hemodynamics, as known in the art, relates to the study of blood flow. The circulatory system, including the heart, the arteries, the microcirculation, and the vein, functions to transport the blood to deliver $O_2$, nutrients and chemicals to the cells of the body, and to remove the cellular waste products. The heart is the driver of the circulatory system generating cardiac output (CO) by rhythmically contracting and relaxing. This creates changes in regional pressures, and, combined with a complex valvular system in the heart and the veins, ensures that the blood moves around the circulatory system in one direction. Hemodynamic parameters (or properties), as described herein, include the physiological conditions associated with the blood flow, which includes not only the physical characteristics of the blood flow itself, e.g., blood flow rate, blood flow pressure, and pulse rate, but also those parameters relating to the blood components such as cells, proteins, chemicals, etc.

The vital signs to be monitored as contemplated in the disclosed embodiments can include, but are not limited to, ECG (electrocardiogram), EEG (electroencephalogram), EMG (electromyogram), EOG (electrooculogram), ERG (electroretinogram), temperature, pulse oximetry, oxygen saturation, oxyhemoglobin saturation, blood component concentration (e.g., glucose level, lipid level, cholesterol level, triglyceride level, levels of different salts, concentration of different types of cells, concentration of blood proteins such as thrombin, cancer markers, heart failure markers), renal function test components (e.g., concentration of albumin, urea, and creatinine in the urine), liver function test components, organ functions, blood pressure (such as atrial pressure, ventricular pressure, pulmonary artery pressure, systolic pressure, diastolic pressure, etc.), blood velocity, respiration rate, pulse rate, (end tidal) $CO_2$ level, blood drug concentration, organic or inorganic substance concentration in the blood (e.g. uric acid, vitamins, heavy metals, carbon monoxide, bacterial toxin), cardiac output, heart rate, heart rhythm, heart rate variability, pH, pathogens, motion, weight, etc. Additionally, the system can be used to monitor migraines, a patient's galvanic skin response, and responses to electrical nerve and muscle stimulation, etc. Depending on the types of underlying physiological conditions to be monitored, the sensing component can include, but is not limited to, an electrochemical detector (such as an needle electrode galvanic electrode or a band electrode for detecting a surface potential or current), an electromagnetic detector (e.g., an optical detector such as an infrared detector and visible light detector, as well as an x-ray detector, gamma-ray detector, etc.), a thermal detector, a pressure detector, an ultrasonic detector, a chemical detector, a magnetic detector, an x-ray detector, an accelerometer, a gyrometer, a motion detector, etc. Other detectors in emerging sensor technology, such as laser Doppler, paper sensors, sensor tattoos, etc., can also be used.

Further, each wireless sensor includes a communication component configured for wireless communication with other sensors. For example, the wireless electrodes described in U.S. Pat. No. 7,979,111 (including the transmitting circuit, such as the remote telemeter 52), can be such a wireless sensor. A wireless sensor can include a mote as described in the above patent, or can include a fully integrated and functional communication circuit that includes an amplifier, a processor, a memory, a battery, and an RF module. Each or selected ones of the wireless sensors can further include a memory of suitable size (for example, 4 GB or 8 GB, to store a large volume or size of relevant medical records of a patient), a data processor, power supply, etc.

In some embodiments, the wireless sensors form a mesh network, where each sensor (also referred to as a "node", "sensor node" or "regular node" hereinafter) not only captures and disseminates its own data, but also serve as a relay for other nodes, that is, the nodes in the mesh network collaborate with each other to propagate the data in the network. In certain embodiments, the mesh network further includes one or more control nodes (or master nodes), which communicate with selected or all of the regular nodes. The master nodes can serve as a data acquisition, processing, and command center, and will be further described below. In other embodiments, the wireless sensors communicate only with each other, e.g., for purpose of synchronizing signal acquisition. In further embodiments, the wireless sensors communicate only with an external control node, but do not communicate with each other or form a mesh network.

The wireless sensors or the network of the wireless sensors can continuously monitor selected vital signs of the subject, and communicates the signals acquired from the sensing components via the communicating components of the sensors to a control or master node. Each of the wireless sensors can be programmed such that signals detected by the sensor falling into a predetermined (e.g., an acceptable or normal) range are not transmitted, or transmitted at a lower frequency. The acceptable range for signals for different patients and for each wireless sensor can be set individually, for example, based on the type of the sensor, the patient's condition, the therapy being used by the patient, etc. As described herein, the control or master node includes a communication component configured to wireless receive signals from each of the plurality of wireless sensors, and send data and/or command to each of the plurality of wireless sensors. The control or master node can further include a monitoring unit coupled with the communication component. For example, the monitoring unit can include a readable medium and a processor coupled to the computer readable medium. The computer readable medium can store coded instructions for execution by the computer processor, which, upon the execution of the instructions, carries out pre-designed tasks.

In some embodiments, the master node of a mesh network can be a PC or workstation computer equipped with a communication component, such as a dongle, for communicating with the wireless sensors. The master node can also include a portable device having a processor, a memory, a display and/or other audiovisual output capabilities to present information to a user, and capabilities of wirelessly communicating with the wireless sensors. In other examples, the master node can include a commercial portable computing device, such as a smart phone (e.g., an iPhone, an Android-based phone, a Windows Mobile-based phone, etc.), a tablet (such as an iPad, a Samsung Galaxy Tab, Google Nexus 7 or 10, etc.), or other similar devices. In further examples, the control and communication capabilities of a master node can also be implemented on one or more regular nodes to "upgrade" such regular nodes into "super nodes" that include both sensing capabilities and the functionalities of the master node as discussed herein.

In the following, wireless sensors including ECG electrodes suitable for acquiring electrophysiological signals related to cardiac function are used for illustrating the operating principles of the sensors and the network formed therefrom. In these sensors, each of the sensors include one or more electrodes which can acquire data related to the quality of the ECG signal, such as the amplitude of a detected voltage, a detected current, and/or electrical skin resistance, and transmit such data to other sensors or the master nodes. The ECG electrodes may be incorporated into a single unit, or they can utilize off-the-shelf snap connector ECG electrodes to adhere to the thorax and to electrically connect to the skin.

In ECG applications, multiple wireless sensors are typically required, which are placed on the patient's body in predetermined locations. As will be further discussed below, these wireless sensors can further self-configure into a set or group which wirelessly sends diagnostic quality ECG signals in a synchronous fashion to a master node, which can derive or synthesize ECG spectrum for display or other forms usable by a physician (or other users) based on the transmitted ECG signals. These sensors can also be configured to send and/or receive signals to/from the master node when a proximity criterion is satisfied, e.g., when the master node is within a predetermined distance from the wireless sensor, e.g., within 3 feet.

For illustration purposes and not limitation, a mesh or pseudo-mesh network formed by a plurality of sensors can be represented by a schematic block diagram as shown in FIG. 1. The illustrated network consists of six sensor nodes and a single master node 110. The sensor nodes can be divided into three clusters: cluster 120 (including node 1 and node 6), cluster 130 (node 2 and node 5), and cluster 140 (node 4 and node 9). The arrows in FIG. 1 represent communication paths between the nodes. As depicted in this example, the network supports at least two modes of communication: (1) communication between the master node and each of the nodes, and (2) communication between nodes. Such a configuration allows for the sensor nodes make their own decisions and reconfigure the network independently of the master node. The wireless communication within the mesh network can be based on proprietary communication stacks utilizing the principles of time domain multiple access (TDMA), with frequencies selected from various MICS bands (Medical Implant Communications Service frequencies) or from the ISM (Industrial, Scientific, and Medical frequency bands (900 MHz, 2.4 GHz, or 5.8 GHz)) as would be appreciated by one of ordinary skill in the art.

For wireless sensors that are configured to detect ECG signals, examples of which are described herein, the sensors can be attached to the skin of a patient for ECG signals recordation in a manner that is similar to the configuration of traditional 3-lead, 5-lead, or 12-lead ECG leads. In certain embodiments, the wireless sensors can be arranged in one or more groups of electrodes each arranged in an orthogonal configuration, such as those illustrated in FIGS. 2A and 2B.

Figure 2A:
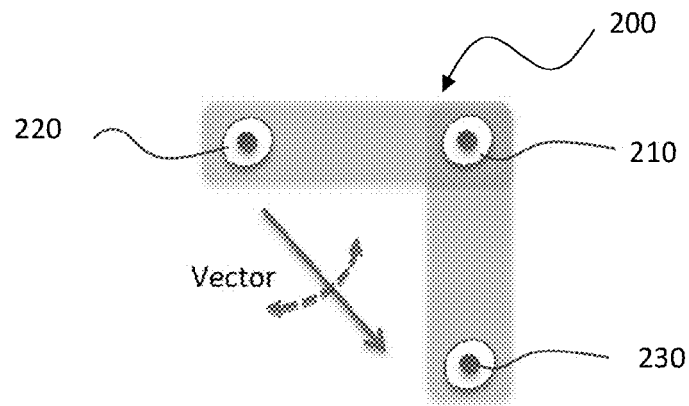
FIG. 2A is an illustrative depiction of an orthogonal configuration of three electrodes (tripole) of a surface-attached node according to an embodiment of the present invention.

As shown in FIG. 2A, a surface node 200 can include three electrodes 210, 220, and 230 (cross-sectional view, each circle representing the center position of each electrode contacting the skin) attached on the skin in an orthogonal configuration. The three electrodes are disposed near the distal end of a star-shaped substrate or pad, which can be made of polymeric materials, fabric, or other materials. As is well known, an ECG measures the voltage resulting from electrical currents conducting through the heart in the vector of the two ECG electrodes making the measurement. When the vector of the ECG is exactly the same as the vector of conduction, the signal reaches maximum, and when the vectors are orthogonal, the signal is zero. The conduction angles may vary from person to person and change with body position and breathing. A tripole sensor as shown in FIG. 2A measures signals on two vectors that are orthogonal to one another, channel 1 between electrode 210 and electrode 220, channel 2 between electrode 210 and electrode 230 (i.e., electrode 210 is common to both channels).

Figure 3:
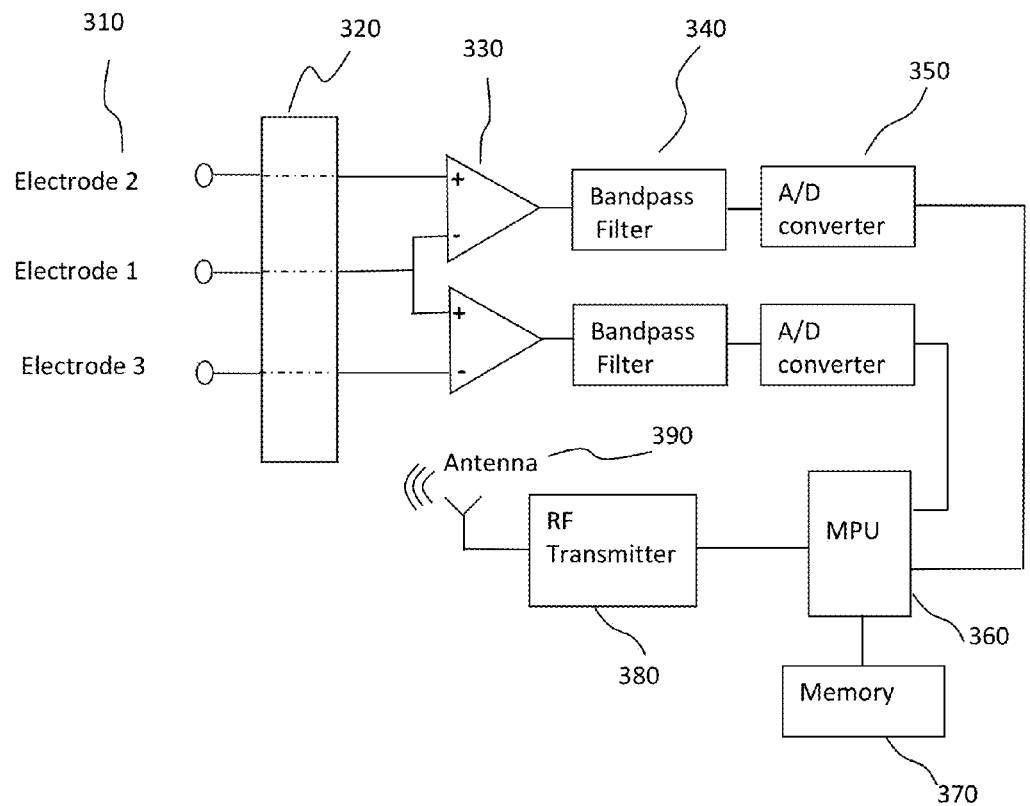
FIG. 3 depicts a block diagram for electrical design for a tripole sensor as shown in FIGS. 2A and 2B, in accordance with one embodiment of the present invention.

An example block diagram of the structure of such a tripole sensor is illustrated in FIG. 3. The three electrodes 310 are connected to instrumentation amplifiers 330 via input protection circuit 320 that protect against electric shock and radio frequency interference. The instrumentation amplifiers 330 measure the difference between its two inputs and amplify that with a gain, e.g., of approximately 10. The amplified signals are filtered by bandpass filters 340 (typically to the frequency response of 0.05 Hz to 60 Hz or alternatively 100 Hz or 150 Hz). Additional gain can be provided in the bandpass filter stage to reach a total system gain of approximately 300. This results in input range of approximately 10 mV between any pair of electrodes. The individual channel signals can then be digitized by A/D converters 350. The converters' resolution may be 12 bits or 16 bits. The digitized ECG signals are passed through the micro processing unit (MPU) 360. The processed signals may be stored on board in a memory 370 coupled with the MPU 360, e.g., a flash memory. Additionally or alternatively, the processed signals can be sent to an RF transmitter 380 and transmitted via an antenna 390 to, directly or indirectly, to an external device (not shown), e.g., a smartphone, a tablet, or a computer.

The configuration of the tripole sensor as shown in FIGS. 2 and 3 do not include a ground electrode. However, a ground electrode can be added as a fourth electrode if needed or desired (e.g., to reduce artifact). Each of the electrodes shown can be attached to the skin of a patient using common electrode technology, such as silver/silver chloride (Ag/AgCl) "floating" electrodes which are attached to the skin of the patient via electrode gel (with a base of a foam pad, a cloth, etc. with medical grade adhesive) to facilitate ionic conduction.

The signals acquired from the two orthogonal channels can be combined using vector mathematics to obtain a signal corresponding to any desired vector angle. This can be used to optimize the measurement of any particular waveform signals of interest, thereby assist in detecting various heart conditions. For example, the absence of P wave can be an important characteristic for diagnosis of atrial fibrillation. As P waves are typically very small, improving signal to noise ratio can be crucial. For example, the presence of p waves can be confirmed by adjusting the vector angle to coincide with the axis of depolarization of the atrium, which coincides with maximum amplitude of the p wave. This can overcome the problem known to those skilled in the art that some patients exhibit very small p waves in the standard ECG vectors.

Adjusting the vector angle of the combined channel can also be used to confirm the absence of p waves in certain conditions such as atrial fibrillation. For example, the vector angles can be incremented in an attempt to detect the presence of p waves, which are seen as a deflection in the ECO typically 0.12 to 0.20 seconds prior to the R wave. If the deflections are not seen in multiple beats of all angles then the absence of the p wave can be confirmed. The vector angle can also be adjusted to find maximum R wave amplitude, which can improve the accuracy of detecting the time of the R wave peak, leading to improvement in the measurement of R to R interval, which is a feature important to the detection of atrial fibrillation because in atrial fibrillation the R to R interval varies chaotically. It is important to distinguish true R to R variability due to noisy measurement of the interval. As another example, S-T segment of a patient's ECG waveform can also be optimized, which is relevant to myocardial infarction (MI) and myocardial ischemia. Those skilled in the art will appreciate that other ECG features and cardiac conditions can be optimized with this technique.

Figure 2B:
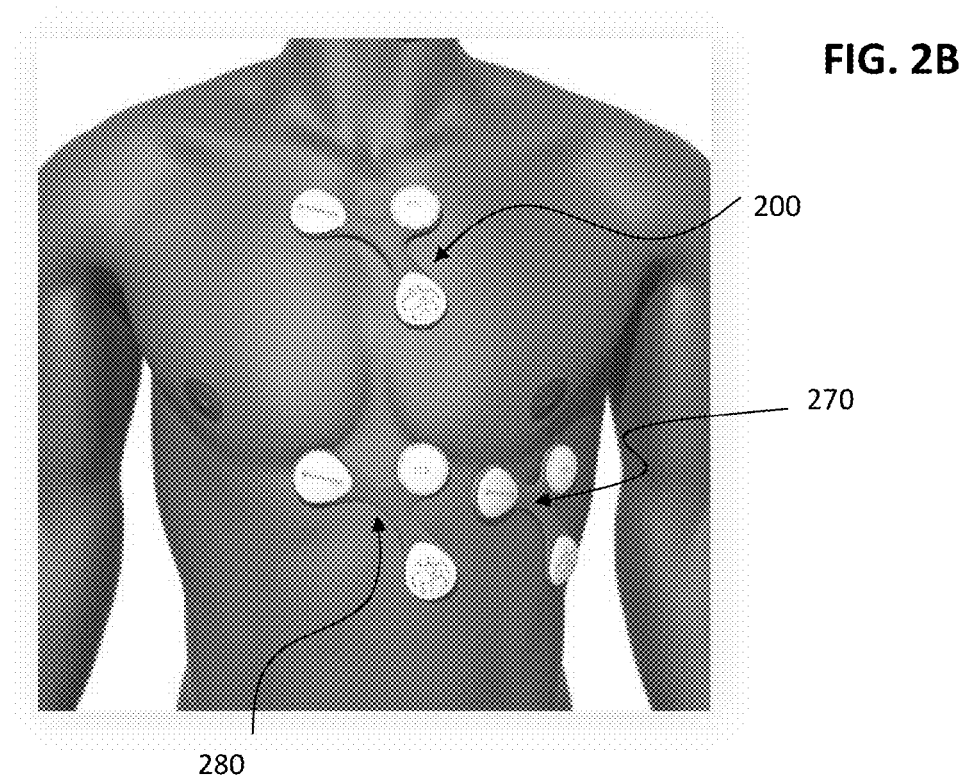
FIG. 2B is an illustrative depiction of an arrangement of multiple surface-attached nodes each having a tripole configuration on the body of a patient in accordance with one embodiment of the present invention.

In some embodiments, multiple surface nodes can be placed on the skin of the patient. As shown in FIG. 2B, a first surface node can be placed high on the sternum just below the clavicle. This can be advantageous for detection of atrial rhythm, as it is nearest the heart's atria, affording the best opportunity to monitor atrial fibrillation. There is less muscle in this location to contaminate the ECG with any electromyogram (EMG) artifact, and it can be on a tissue that is less likely to move and contaminate the ECG with motion artifact. An optional second surface node 270 may be added nearest the ventricles. Two electrodes of this group can be at locations V4 and V5 of a standard 12-lead ECG, and the third a proxy for the left leg location. The signals from the two surface nodes may be combined in various ways to provide a faithful representation of a standard 3, 5, or 12 lead ECG. The second surface node can also be able to measure ventricular ischemia due to blockage of the major vessels. An optional third tripole surface node 280 may be further added to provide enough signals to derive a full 12-lead ECG.

In a system where there are more than one wireless sensors (as shown the three tripole sensors shown in FIG. 2B, all of the wireless sensors can each individually transmit the collected physiological data to an external device (e.g., a monitoring device as described herein). Alternatively, one of the wireless sensors can include hardware and software necessary to serve as a master node or gateway that receives detected physiological data from other wireless sensors, and forward such signals via a radio or WiFi link to the external monitoring device at an appropriate rate (e.g., to save battery power of the sensors). The transmission can also be optionally compressed with little or no information loss. The transmitted physiological data can be processed by the monitoring device with appropriate program, or can be further uploaded to a server for processing and/or analysis, which are described further below.

Figure 4:
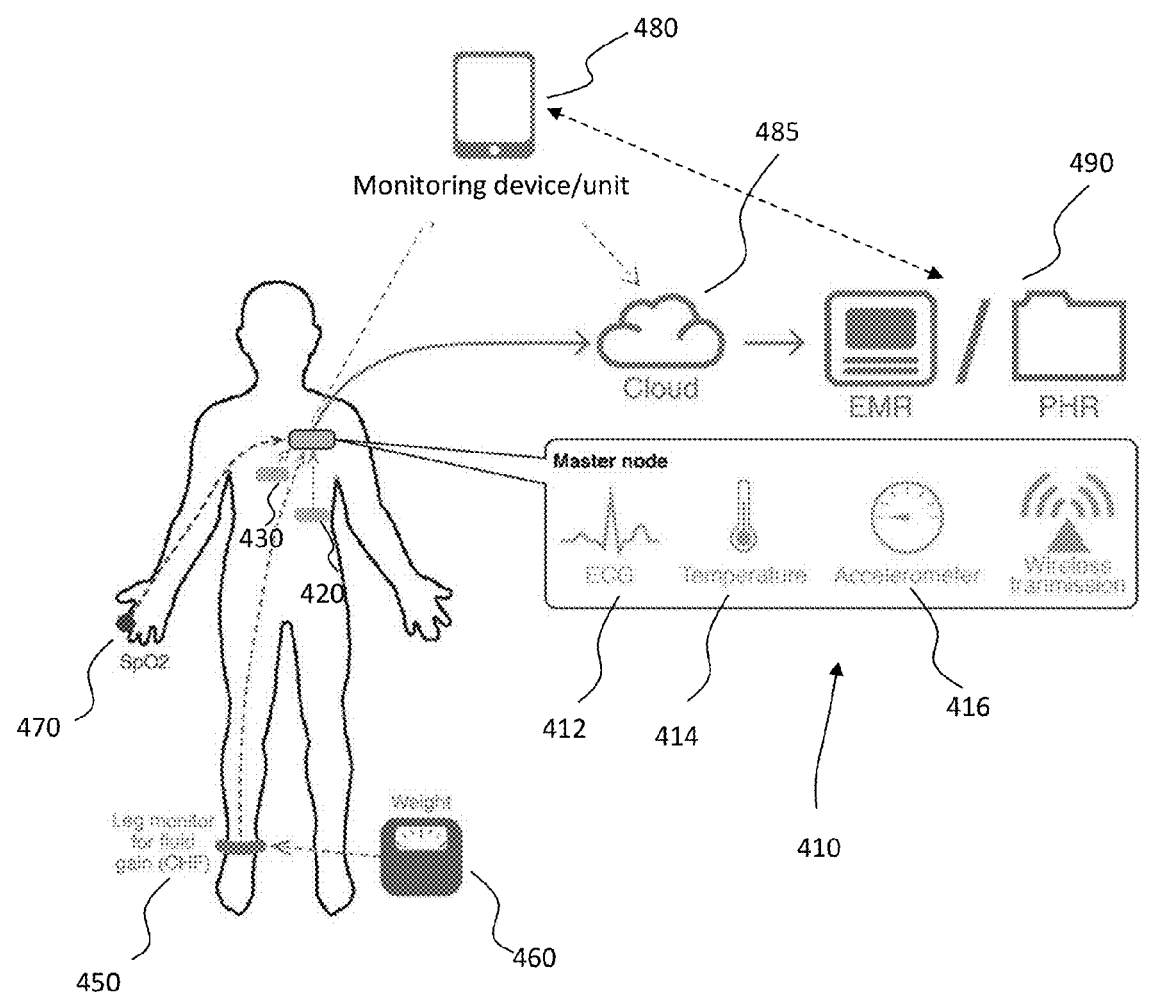
FIG. 4 depicts various types of wireless sensors as attached on a patient and their communications with a monitoring device and a server, in accordance with one embodiment of the present invention.

Further, the wireless sensors according to one embodiment of the present invention can include different sensing components for monitoring a plurality of different vital signs. For example, one sensor can include a pressure detector for monitoring the pulse rate, and another sensor can include an electrochemical detector for blood glucose level measurement (the glucose level can also be measured by an infrared detector or eye scanner). For another example, one wireless sensor can include a surface-attached sensing component, such as one or more ECG electrodes, and another sensor can include an implantable sensing component, such as an implanted intracardiac pressure transducer coupled to a heart chamber (e.g., the right ventricle). Thus, wireless sensors of different types for monitoring different vital signs can be conveniently worn by or implanted in the patient depending on the needs of care for the patient. For purpose of illustration and not limitation, FIG. 4 depicts the use of different types of wireless sensors, including three surface-attached nodes 410, 420, 430 (each containing an ECG sensor, e.g., the tripole sensors described herein), weight sensor 460, leg monitor sensor 450, and oxygen saturation (SpO$_2$) sensor (such as pulse oximeter worn on a patient's finger) 470 which can also be used to monitor ECG. Additional sensors (not shown) can include a wrist sensor or a pendant that can be used for monitoring heart rate, blood pressure, temperature or other hemodynamic properties. Node 410 includes an ECG sensor 412, a temperature sensor 414, and an accelerometer 416, as well as a wireless transmission module. Thus, node 410 can serves as a master node to receive ECG measurement signals sent by nodes 420 and 430 as well as the signals from other sensors, and wireless relaying data collected from all the sensors to an external device, e.g., a monitoring device 480 or cloud 485, either of which can be connected to the patient's EMR records. Like Node 410, Node 420 and 430 can also each include other sensors, such an accelerometer, a gyrometer, a temperature sensor, a GPS receivers, etc. (not shown). The real-time monitoring data gathered from the various sensors can be combined with the information from the patient's EMR records to optimize the signal detecting algorithm used by the sensors, and/or to make diagnosis assistance or clinical support decisions, as will be further described below.

The use of hybrid sensors can also provide a caregiver with more comprehensive information regarding the patient's condition in a more efficient and/or more reliable manner. For example, monitoring different vital signs simultaneously using different types of wireless sensors can provide redundancy and improved robustness of monitoring quality as well as facilitate reconciliation of inconsistencies among the data gathered from different types of sensors (for different vital signs), reduce false alarm rates, etc. Certain vital signs can also be considered as having higher priorities (e.g., because the sensors for monitoring these vital signs have higher reliability or accuracy), and as such, the data gathered for these vital signs can be given more weight when data gathered for other vital signs may suggest a different condition the patient is in. In addition, when implanted wireless sensors are used, especially those implanted relatively deep within the patient's body (e.g., in the patient's heart), one or more surface-attached sensors, e.g., those located near the implanted sensors, can be used to relay the signals acquired from the implanted sensors, e.g., to a master node, thereby providing potentially better quality signals for further processing and analysis. For example, for a wireless sensor implanted in a patient's heart chamber, another wireless sensor can be attached at the patient's chest to receive and re-broadcast the signals obtained by the implanted sensor. The wireless sensors can be further used in conjunction with certain medical devices worn by the patient (e.g., rehabilitating devices, robotics, prostheses, etc.), for collecting and transmitting sensed signals as a feedback or input for these devices so as to further enhance their functionalities.

The data collected from different types of sensors can be weighted, ranked, processed, validated, transmitted to an EMR server, and utilized with other data in the EMR of a patient. The ECG and other vitals can be prioritized by the patient disease conditions and health status. For example, an otherwise health patient having AF surgery has a limited set of parameters, whereas a patient just discharged with Congestive Heart Failure (CHF) with co-morbidities of diabetes, and obesity, and multiple medications can be monitored for those vital sign signals relevant to disease specific algorithms based on ECG, blood glucose levels and weight.

For example, the system can store "diagnostic templates" containing threshold levels of specific vital signs, which can trigger a diagnosis when the threshold levels for the vital signs are reached by a patient undergoing monitoring. In response to information patient-specific information, the system can adjust the "diagnostic templates" based on disease-specific risk factors (e.g. heart rate variability in patients having atrial fibrillation) as well as patient-specific risk factors (e.g. fluctuation in blood pressure in patients with hypertension). The system can also differentially weigh different vital signs according to the indication and patient's existing conditions, measure the patient's vital sign variability, trends over time, and deviations from previous states using predetermined statistical models, for example, statistical models that use measurements such as average, standard deviation, and covariance. The data processing and analysis can be performed on the sensor nodes, a monitoring device that is configured to receive the sensor data from the various sensors (or from the gateway sensor node as shown in FIG. 4), or a server connected to the monitoring device.

Figure 5:
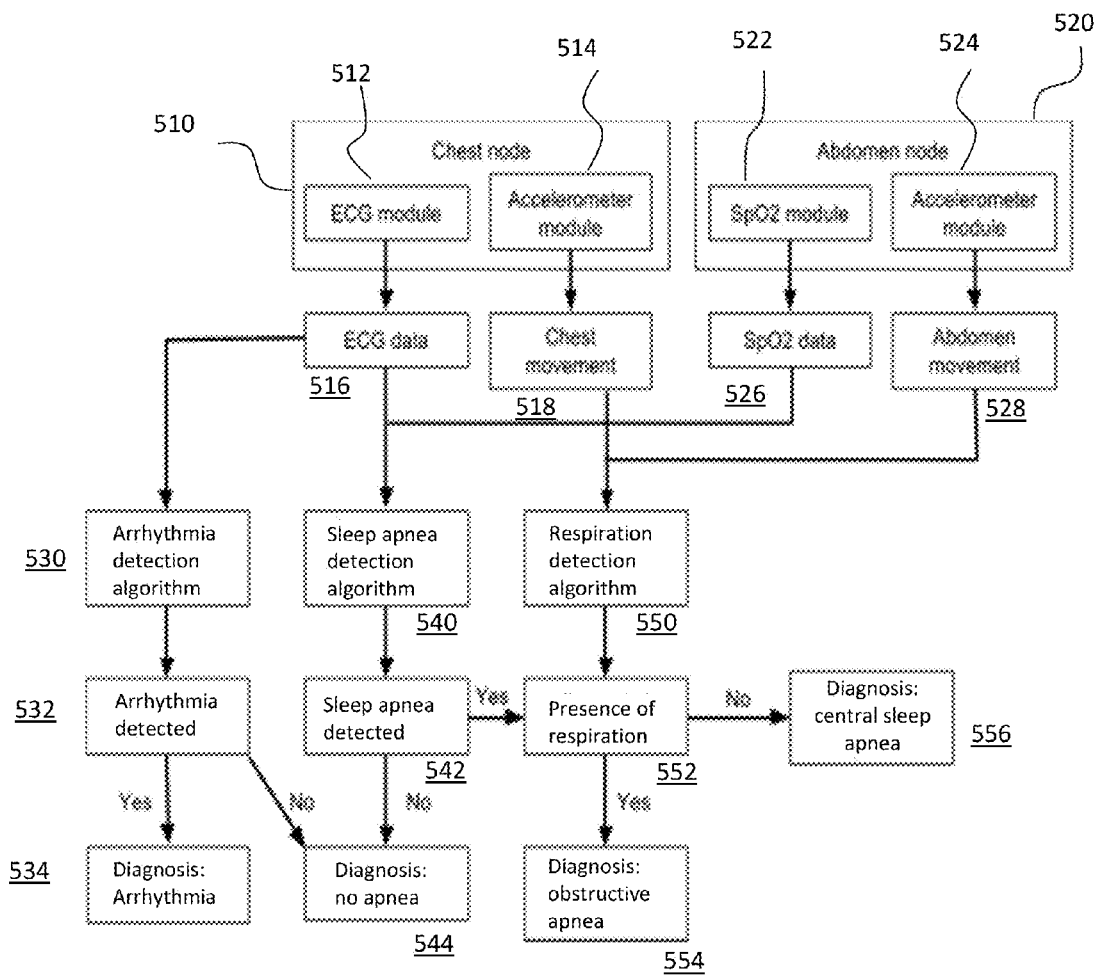
FIG. 5 depicts a flowchart illustrating processes utilizing data from different types of wireless sensors for diagnosing various conditions of a patient, in accordance with one embodiment of the present invention.

In an example embodiment, the configuration of different types of wireless sensors as depicted in FIG. 5 can be used to diagnose various conditions of a patient. The chest node 510 includes an ECG module/sensor 512 and an accelerometer module 514, and abdomen node 520 includes $SpO_2$ module/sensor 522 and an accelerometer module 524. The ECG measurement data 516 can be used as an input for an arrhythmia detection algorithm 530. When arrhythmia is detected at 532, it can be determined that the patient has arrhythmia at 534. In addition, the ECG data 516 together with the $SpO_2$ data 526 can be used an input for a sleep apnea detection algorithm 540. When apnea is not detected at 542, and there is no arrhythmia detected, a diagnosis of no apnea is reached at 544. Chest movement data 518 and abdomen movement data 528 from the accelerometer modules 514 and 524, respectively, can be used together as input for a respiration detection algorithm 550. When the presence of respiration is detected at 552 based on the respiration detection algorithm and the detection of sleep apnea, the patient is diagnosed as having obstructive apnea 554. When the presence of respiration is not detected (while sleep apnea is detected), the patient is diagnosed as having central sleep apnea at 556.

In certain embodiments, the present invention provides a system for monitoring a heart condition for a subject (or a patient) using an implantable cardiac device in combination with one or more wireless sensors suitable for attachment to the skin of a subject for monitoring the patient's ECG. In such a manner, the electrograms (EGM) obtained by the internal electrodes of the implantable cardiac device (which are subject to positioning errors or failure and difficult to adjust or replace) can be cross-checked with the ECG signals collected from skin-attached wireless sensors or nodes (which are more robust in positioning stability and easier to adjust/manipulate), thereby improving the confidence and accuracy of detection and management of certain heart conditions by implantable devices.

In some embodiments of the invention, the implantable cardiac device can include an ICD, a single or multi-chamber pacemaker, a cardiac resynchronization therapy device, and other implantable electronic devices that are capable of monitoring, intervening, or influencing the electrical system of the patient's heart. It is understood that modern-day ICD can be designed to perform functions of conventional pacemakers, and therefore ICD can represent a broader category of implantable cardiac devices.

In some embodiments of the invention, the one or more wireless sensors (e.g., surface sensor(s), surface node(s)) can each include a sensing component configured to detect ECG signals. Additionally, the wireless sensors can include a communication component configured to wirelessly transmit the detected signal or other information to other surface nodes, as well as wirelessly receive detected signal or other information from other surface nodes. Selected surface nodes can also wirelessly communicate with the implantable device. In some embodiments, selected surface nodes can also receive signals transmitted from the implantable device. For example, the wireless sensors can be used to detect one or more of heart conditions based on ECG signals, such as ventricular and atrial arrhythmias including but not limited to ventricular fibrillation, ventricular tachycardia, atrial fibrillation, and bradycardia. The implantable device and the surface nodes can interact with each other on a number of different ways, such as: (1) the surface nodes provide diagnostic information to the implantable device which can use such information to make adjustments in its operation; (2) the surface nodes and the implantable device exchanges information such that the operations of both the implantable device and the surface nodes can be affected by each other; and/or (3) the surface nodes actively participates in the monitoring/treatment decision making, e.g., in determining whether and when to administer a therapy to the patient (such as shock or pacing) to influence the electrical system of the heart so as to address the detected condition. The implantable device can include a communication component to wirelessly transmit information to, and/or receive information from one or more of the surface nodes, as will be further described below, where the communication can be conducted through RF, magnetic, acoustic, electrical, optical, and other transmission means as appropriate. The implantable device can also include software configured to process information received from the sensor of the implantable device and the information received from the surface nodes, as well as components for administering the therapies appropriate to address the heart conditions detected.

In certain embodiments, additional components, such as a remote or central server, can be used to make such a diagnostic/treatment decision based on information received from the implantable device and the surface nodes. Again, the implantable device can be used to execute the action corresponding to the decision made with the information provided by the surface nodes.

In some embodiments, the surface-attached wireless sensors include ECG electrodes suitable for acquiring electrophysiological signals related to cardiac function are used for illustrating the operating principles of the sensors and the network formed therefrom. In other embodiments, the surface-attached wireless sensors can include one or more tripole sensors, as illustrated in FIGS. 2A and 2B, as discussed above.

In some embodiments where a plurality of wireless sensors are employed, the wireless sensors can be configured to form a network which can be use a routing strategy such as star, mesh, pseudo-mesh, or any other routing topology. The network can include one or more master nodes or other devices which can receive signals from the wireless sensors and have additional signal processing, decision making, and other supervising or coordinating functionalities. The master node(s) or other devices do not need to be attached to the patient's body. For example, the master code can be a desktop or laptop PC, a tablet, a smartphone, etc., as discussed above.

In some embodiments, one or more surface-attached sensors, e.g., those located near an implanted cardiac device, can be used to relay the signals acquired from the implanted sensors, e.g., to an external monitoring device, thereby providing potentially better quality signals for further processing and analysis. For example, for an ICD, a wireless sensor can be attached at the patient's chest to receive and resend the signals obtained by the implanted sensor of the ICD.

Figure 6:
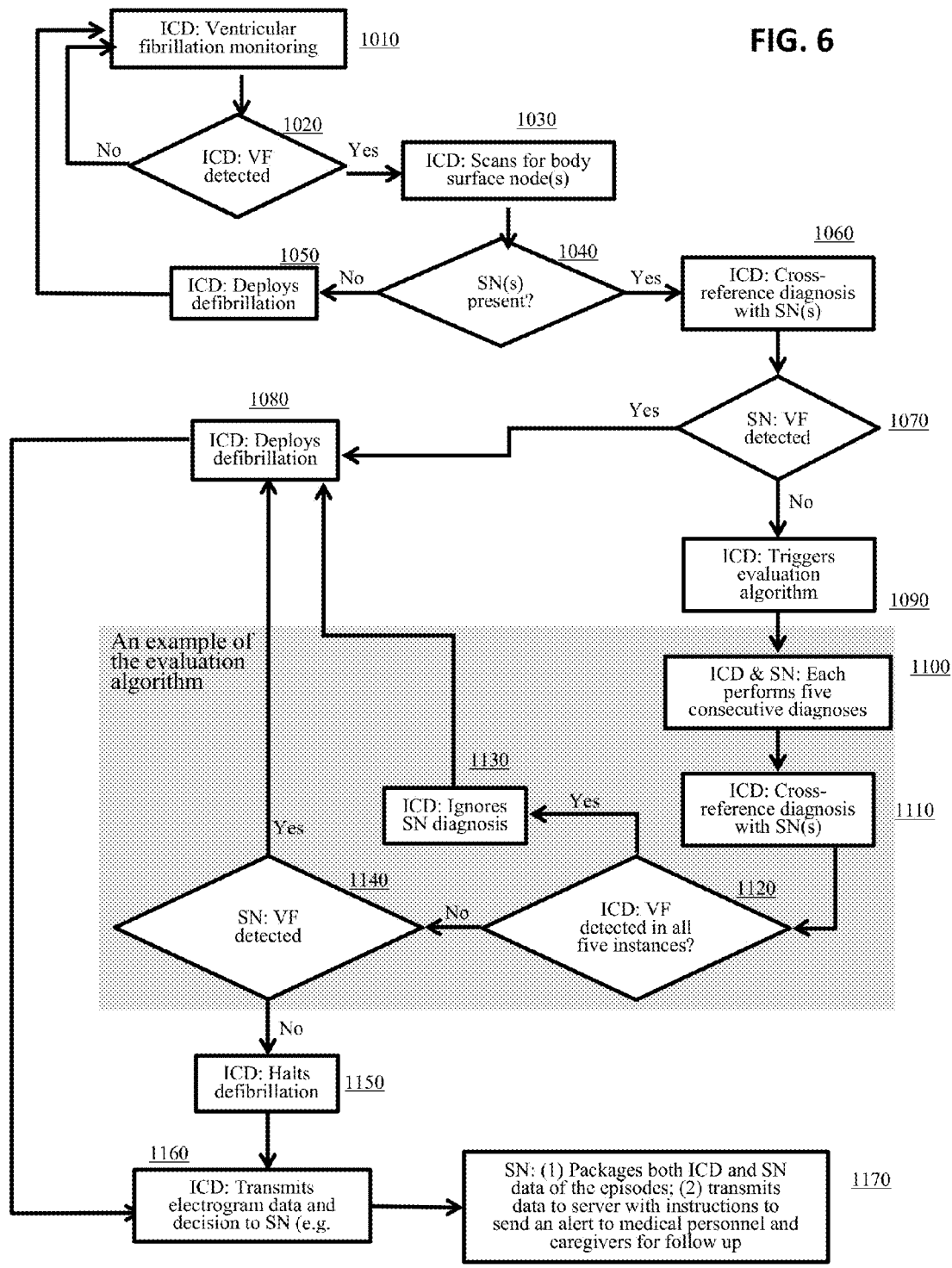
FIG. 6 is an illustrative flow chart for a process of monitoring and managing ventricle fibrillation using an ICD and surface-attached wireless sensor(s) in accordance with one embodiment of the present invention.

FIG. 6 illustrates the operations of a system including an ICD and one or more surface nodes (SNs) in accordance with one embodiment of the invention. During step 1010, the ICD continuously scans electrogram data to detect ventricular fibrillation (VF). It is understood that VF is used herein only as an example, and other conditions that an ICD typically monitors or manages, such as arrhythmia, tachycardia, etc., can also be addressed by appropriate modification of the process described herein. Accordingly, when VF is used herein, it should be considered as referring to other conditions that an ICD can monitor or manage.

As shown in FIG. 6, If VF is detected in decision block 1020, control flows to Step 1030 and the ICD scans for the presence of surface node(s) on the body of the patient via wireless communications. If no SN(s) is detected by the ICD in decision block 1040, control flows to step 1050 and the ICD deploys a predetermined defibrillation therapy based on the programming of the ICD. If the ICD detects the SN(s), secure wireless link(s) can be set up between the ICD and the SN(s) using, but not limited to, RF, electric, magnetic, acoustic, or optical communication protocol(s) as appropriate. Then, control flows to step 1060 and the ICD cross-references VF diagnosis with SN(s). If the SN(s) also detects VF in decision block 1070 (e.g., by using techniques known in the art), control flows to step 1080 and the ICD deploys a predetermined defibrillation therapy (e.g., by administering a shocking current of a predetermined magnitude and duration). If the SN(s) does not detect a VF episode, control flows to step 1090 and triggers an evaluation algorithm in the ICD using weighted or non-weighted data or diagnoses from both the ICD and the SN(s). An example of such evaluation algorithm is a voting system based on diagnoses of both the SN(s) and the ICD. For example, after the algorithm is triggered in step 1090, control flows to step 1100 and the ICD and the SN(s) each perform five consecutive diagnoses using data acquired independently by the two devices. Control then flows to step 1110 and the ICD cross-references diagnoses with the SN(s). If ICD detects VF in all five diagnoses in decision block 1120, control flows to step 1130 in which the ICD ignores the diagnoses by SN(s) and deploys a predetermined defibrillation therapy. If the ICD diagnoses is less than 100% for VF in decision block 1120, the ICD can incorporate diagnoses by the SN(s) in the decision-making. For example, in decision block 1140, if the SN(s) detects any episode of VF, control flows to step 1080 and the ICD deploys defibrillation current. If the SN(s) does not detect any VF in all five episodes, control then flows to step 1150 and the ICD can decide not to administer defibrillation, or administering a defibrillation current with modified parameters (e.g., with a modified waveform, reduced energy, or reduced duration, as desired or needed).

Independent of the final decision, the ICD can further transmit relevant electrogram data and decision of the episode to the SN(s), using, but not limited to, RF, electric, magnetic, acoustic, or optical communication protocol(s) with proper encryption as in step 1160. The control then flows to step 1170 where the SN(s) (or selected SNs from a plurality of SNs) further packages the data from both ICD and SN(s) for the episode and transmits to a remote server using, but not limited to, RF, electric, magnetic, acoustic, or optical communication protocol(s). The transfer of data to the server may route through secured relay station(s). The data package can also contain an alert to the server (in-house or third-party) such that the server can generate a notification for, but not limited to, medical professional(s), caregiver(s) and/or care providers(s). The server also generates an entry documenting the episode to an EMR system.

Figure 7:
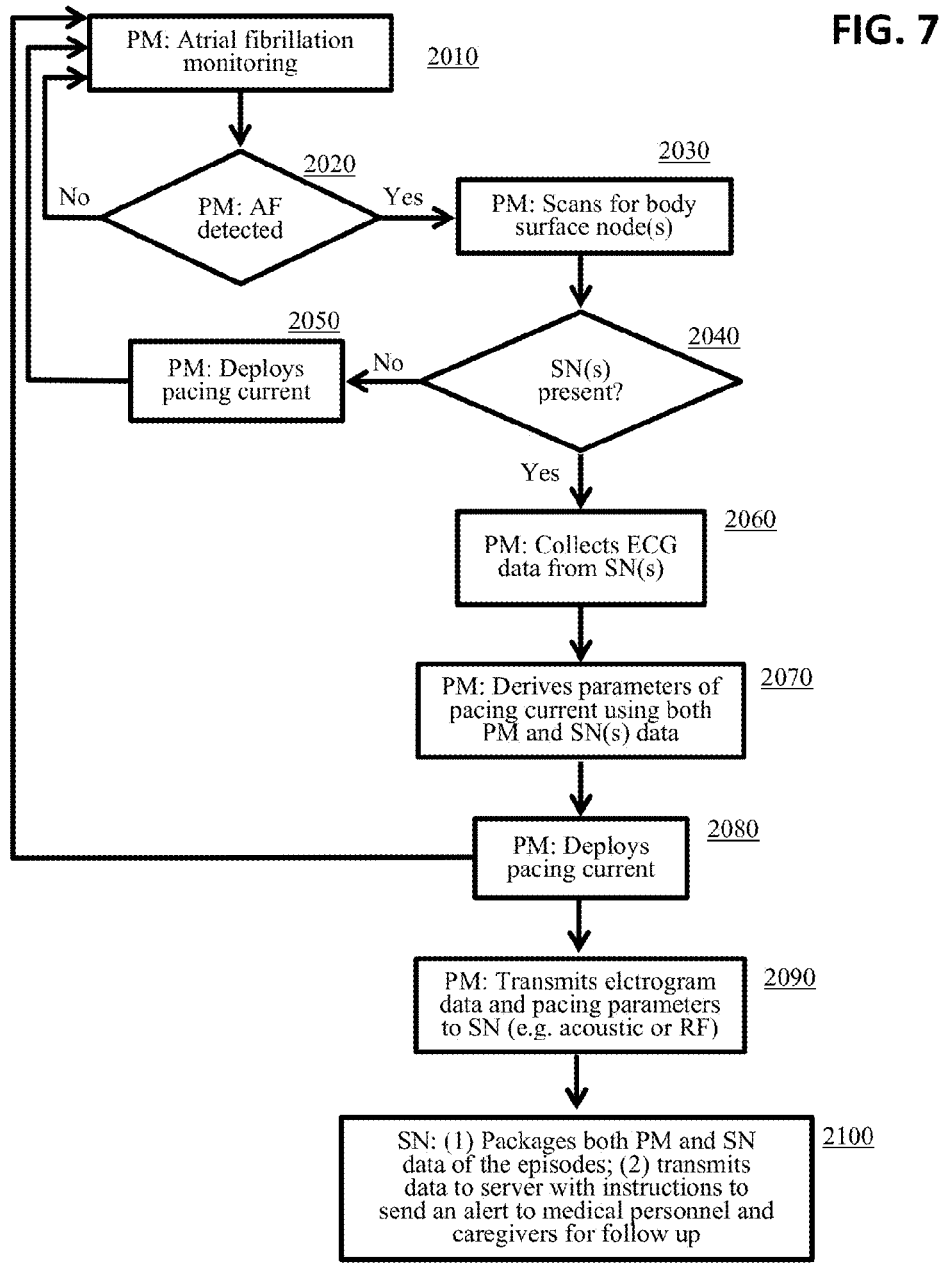
FIG. 7 is an illustrative flow chart for a process of monitoring and managing atrial arrhythmia using a pacemaker and surface-attached wireless sensor(s) in accordance with one embodiment of the present invention.

FIG. 7 illustrates the operations of a system including a pacemaker and one or more surface nodes in accordance with one embodiment of the invention. It is understood that the pacemaker described herein can also be an ICD having the pacemaking capability. During step 2010, the pacemaker (PM) continuously scans electrogram data for atrial arrhythmias that may be a precursor to atrial fibrillation (AF), such as atrial ectopic beats (sometimes referred to as premature atrial contractions or PACs). If one or more PACs are detected in decision block 2020, control flows to Step 2030 and the PM scans for the presence of body surface node(s) via wireless communications that may include, but not limited to, RF, electric, magnetic, acoustic, and optical channel(s). If no SN(s) is detected by the PM in decision block 2040, control flows to step 2050 and the PM determines the parameters of the pacemaking therapy for subsequent deployment. If the PM detects the SN(s), secure wireless link(s) can be set up between the PM and the SN(s) using, but not limited to, RF, electric, magnetic, acoustic, or optical communication protocol(s). Then, control flows to step 2060 and the PM collects ECG data from the SN(s). In step 2070, the PM derives parameters for the pacemaking therapy (such as magnitude of the pacing current, timing of administering the pacing current, etc.) using the data from both the PM and the SN(s). Then the PM deploys administers the therapy in step 2080.

After the pacing episode, the PM can transmit relevant electrogram data and pacing current parameters to the SN(s), using, but not limited to, RF, electric, magnetic, acoustic, or optical communication protocol(s) with proper encryption as in step 2090. The control then flows to step 2100 where the SN(s) further packages the data from both PM and SN(s) for the episode and transmits to a remote server using, but not limited to, RF, electric, magnetic, acoustic, or optical communication protocol(s). The transfer of data to the server may route through secured relay station(s). The data package also contains an alert to the platform (in-house or third-party) such that the server will generate a notification for, but not limited to, medical professional(s), caregiver(s) and/or care providers(s). The server can also generate an entry documenting the episode to an EMR system.

It is understood that in the voting algorithm illustrated above with respect to FIG. 6, the numbers and duration of consecutive diagnoses can be varied as desired or needed. Other schemes of the voting or decision algorithm can be designed. Further, for the processes described in connection with both FIG. 6 and FIG. 7, when information from SN(s) and the implantable device is both available and used in conjunction for the evaluation of the heart condition, the SN(s) and the implantable device can be assigned different weights based on the design and condition of the ICD, the design and configuration of the SN(s), as well as other considerations affecting the relative trustworthiness between the ICD and SN(s) for diagnosing or interpreting the same heart episode. Alternatively, a multivariate optimization approach can be employed by taking into account of information received from the SN(s) and the implantable cardiac device to make a diagnostic conclusion that has the best probability to be correct, and/or derive a set of parameters for the therapy to be administered within the capability of the implantable cardiac device that can best address the episode detected.

According to another embodiment of the present invention, an integrated system is provided for acquiring, transmitting, analyzing, and utilizing vital signs (e.g., hemodynamic parameters, organ functions, blood test results) monitored in real time by wireless sensors worn by the patient together with the patient's medical records for clinical decision support and other patient health care objectives. Such an integrated system includes the wireless sensors and a monitoring unit, and can further include a remote server(s) that stores the patient's EMR data.

As discussed herein, the monitoring unit or device (and/or a remote server connected to the monitoring unit or device) can include a computer program that manages the transmission of the real time data from the wireless sensors, as well as perform certain specified tasks based on the real time monitoring data as well as the patient's EMR, e.g., diagnosing a condition of the patient, alerting the patient or a physician of a diagnosed condition of the patient, making a suggestion for the diagnosis or treatment of the subject, and/or validating a diagnosis or treatment proposed by a physician, etc. The monitoring unit (or a remote server coupled thereto) can further integrate such received real time monitoring data from the wireless sensors with the patient's past medical history and/or other relevant data (e.g., stored demographics, vital signs history, previous diagnosis, medications, allergies, etc.).

The EMR and other relevant data of a patient can be stored in a permanent storage medium (e.g., a hard drive, a solid state drive, a flash drive, or other types of memories) of the monitoring unit, or transmitted from a physician computer or a remote server (such as a remotely located server operated by a healthcare provider, or a cloud server) accessible by the monitoring unit by wired and/or wireless communications. Also, the data acquired and stored by one or more of the wireless sensors can also be asynchronously or simultaneously uploaded to the monitoring unit and/or further to the remote server for long term storage and/or further analysis. In other words, the patient's EMR can be updated continuously or from time to time by incorporating the data gathered by the wireless sensors. Without departing from the scope of the invention, this data can be stored either locally on the sensor or remotely anywhere on the network. For example, selected portion of a patient's medical history in the patients EMR can be retrieved from a remote server or computer to be stored on selected wireless sensors having a storage medium having a sufficient storage capacity such that relevant patient data can be carried around on the wireless sensors worn by the patient and readily accessible in a clinical setting or another setting where the patient medical records are not otherwise available.

The real-time monitoring data gathered and transmitted by the wireless sensors can be processed if necessary to extract clinically relevant information (e.g., as a diagnosis) and formatted for specific EMR systems, and entered into EMR database located on a computer or data server as individual entries and/or file attachments in a format that complies with current regulatory standards. The data transmission frequency, data format, security and other settings can be preset before the wireless sensors are activated, but can made adjustable according to a patient's current conditions detected by the monitoring system and/or clinical information obtained from other sources (e.g., medications, allergies, lab results, past/present diagnoses). For example, the parameters of the monitoring by the wireless sensors can be adjusted in response to updated patient EMR. When the patient's EMR information is updated (including a change in patient conditions or detection of a "health event," updated lab results, changes in/initiation of medications, imaging results, or new diagnosis), the monitoring system can change the protocol of the monitoring, e.g., data transmission frequencies of uploading the wireless data to the monitoring unit, threshold levels for alerts and alarms, etc. As an example, if a patient's EMR is updated to include a new medication (e.g., a beta blocker) that the patient starts to take, the monitoring program installed at the monitoring unit or the remote server can decide if the patient monitoring protocol needs to be altered. If the patient having a low heart rate, a beta blocker can make the patient prone to develop bradycardia. In this case, the monitoring system can adjust the transmission frequencies of the heart rate appropriate to monitor signs of bradycardia.

In addition, a list of the medications (and their dosages) that have been prescribed to the patient may be stored in the patient EMR with the schedule for taking them. The monitoring system can also access the patient EMR and download the medications, their dosages, and schedule in order to provide alerts (e.g., sound or vibration alarm, text message, or other types of notification) to healthcare professionals or the patient. If the medications or schedule are changed in the patient EMR, then notifications can be sent to the monitoring system and the alert schedule can be updated accordingly. Additionally, the monitoring unit can also make determination, based on the data received from the wireless sensors, whether the patient has been taking the medications, and/or the correct dosages of medications as prescribed by physicians. The monitoring program can be configured such that a detected noncompliance by the patient can trigger alerts or notification to the patient, as well to the responsible physicians. In this way, the monitoring system could also act as a "compliance monitor."

It is noted that the diagnosis may be based on both the transmitted data from the wireless sensors and the patient's existing EMR (i.e., before the EMR is updated to incorporate the new diagnosis).

Figure 8:
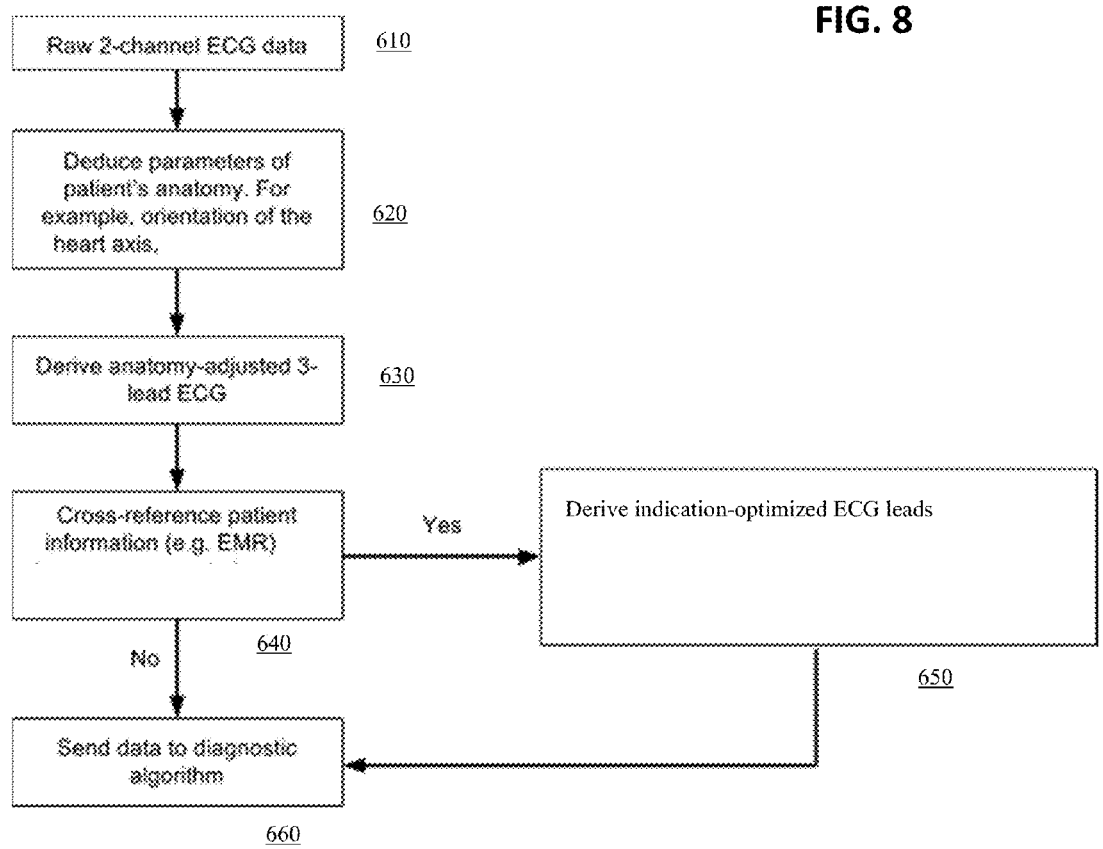
FIG. 8 depicts a flowchart illustrating a process for personalized ECG monitoring of a patient according to an embodiment of the present invention.

FIG. 8 illustrates a method for personalized ECG monitoring of patient conditions according to an embodiment of the present invention. Using a tripole ECG sensor described previously as an example, the raw two-channel ECG data is acquired at 610, and may be used to derive parameters of the patient's anatomy, e.g., orientation of the ventricular and/or atrial heart axis, at 620. At 630, anatomy-adjusted 3-lead ECG can be developed. At 640, the patient's EMR is cross checked for known or suspected cardiac complications, or absence thereof. If there is anything in the patient's EMR that shed light on or is inconsistent with the ECG data, the ECG data can be modified to take that information into account at 650. The result of the modified ECG data to a diagnostic algorithm at 660.

Figure 9:
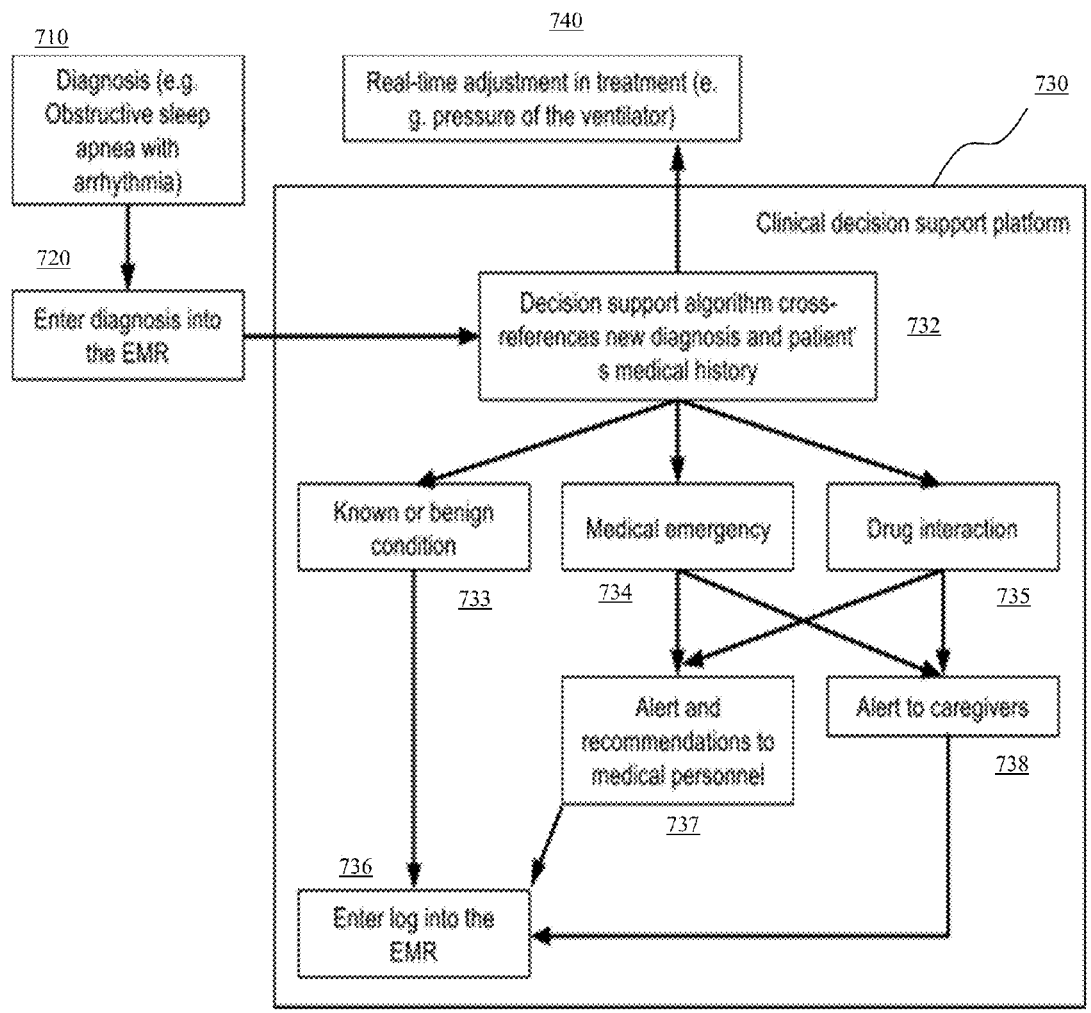
FIG. 9 depicts a flow chart illustrating a process utilizing the result of a diagnosis based on data from wireless sensors as well as the patient's existing EMR for clinical decision support according to an embodiment of the present invention.

Additionally, after the patient EMR is updated, the monitoring program can reevaluate the patient's condition and decides if additional actions to be performed (e.g., if certain alerts are be sent to appropriate recipients or if the monitoring protocol has to be adjusted. FIG. 9 illustrates an example method utilizing the result of a diagnosis based on data from wireless sensors as well as the patient's existing EMR for clinical decision support according to an embodiment of the present invention. At 710, a diagnosis is made by the monitoring program based on data received from wireless sensors (e.g., by the algorithm described in connection with FIG. 4). At 720, the diagnosis is automatically (without a user's assistance or intervention) entered into the patient's EMR. The new diagnosis and the patient's medical history are together used in a clinical decision support platform 730, which include a decision support algorithm 732. The decision support algorithm cross-references new diagnosis and patient's medical history to determine whether the patient's current condition is a known or benign condition (at 733), a medical emergency (at 734), or a drug interaction (at 735). Based on the result of determination, different actions can be performed (e.g., alerts to be sent to medical personnel at 737, alert to be sent to caregivers at 738, and logging the evaluation result into the patient EMR at 736). Additionally, the decision support algorithm can adjust, in real-time, parameters of any treatment that is currently being given to the patient, such as the pressure of the ventilator, at 740.

Figure 10:
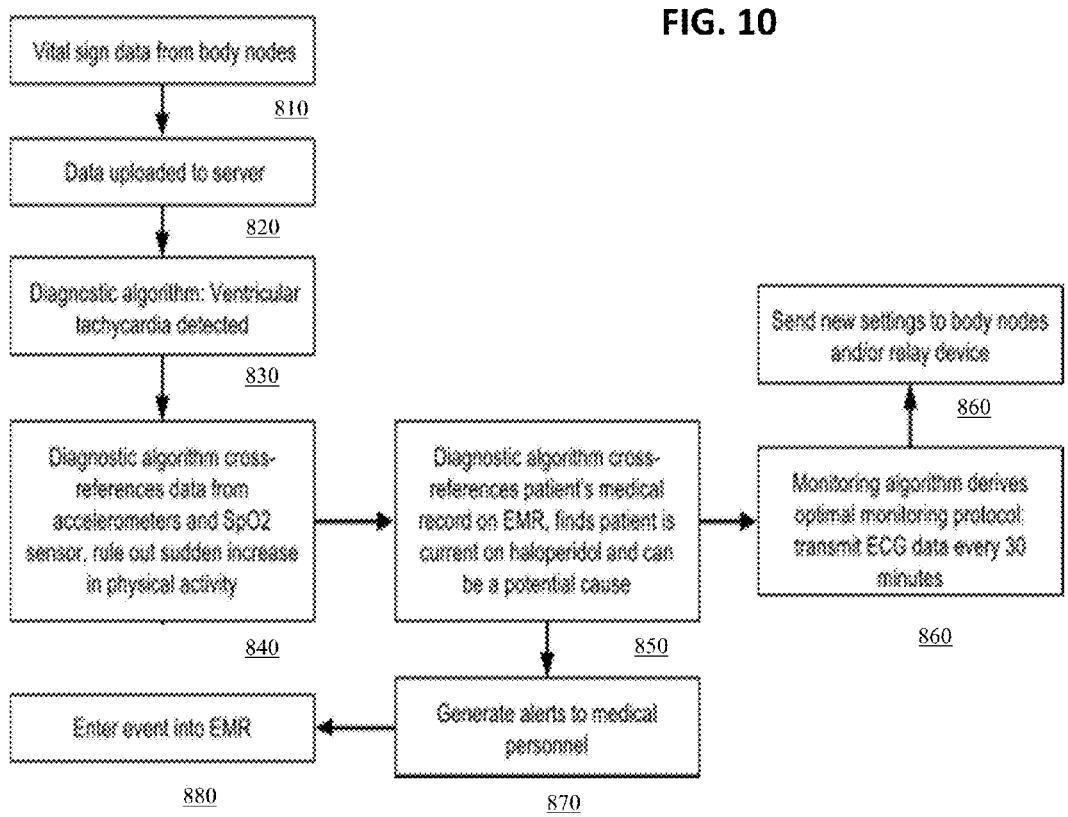
FIG. 10 depicts a flow chart illustrating an example method utilizing the result of a diagnosis based on data from wireless sensors as well as the patient's existing EMR for determining a cause for the diagnosis and updating the monitoring protocol according to an embodiment of the present invention.

FIG. 10 illustrates an example method utilizing the result of a diagnosis based on data from wireless sensors (e.g., shown in FIG. 4) as well as the patient's existing EMR for determining a cause for the diagnosis and updating the monitoring protocol according to an embodiment of the present invention. At 810, vital sign data are collected from wireless ECG sensors attached to the skin of a patient. At 820, the vital sign data are transmitted from the wireless sensors (or selected relay sensor or sensors as described above) to a server (e.g., a monitoring unit, a physician computer, a cloud server, etc.). At 830, the uploaded data are processed by a diagnostic algorithm and a particular condition (e.g., ventricular tachycardia) is preliminarily diagnosed as a result. At 840, the diagnostic algorithm further cross-references the data from accelerometers and SpO$_2$ sensor, and rules out sudden increase in physical activity. Further, the diagnostic algorithm cross-references patient's EMR and determines what may be associated or a cause for the detected condition (e.g., a haloperidol medication being taken by the patient). Accordingly, the medical personnel is notified or alerted with the appropriate message at 870, and the diagnostic event is entered into the patient's EMR at 880. Also, the monitoring protocol or settings can be updated at 860 based on the determined cause of the condition (e.g., the frequency of transmitting ECG data is updated to be 30 minutes), and the new settings are sent to the wireless sensors or relay sensor(s) at 860.

As additional examples, the integrated monitoring system can allow a physician to provide a correct diagnosis of symptoms exhibited by a patient and detected by the wireless sensors. For example, although oxygen saturation for a healthy person is 90-100%, for a patient having a chronic obstructive pulmonary disease, the "normal" oxygen saturation is much lower. Thus, if the patient has an oxygen saturation level of lower than 90% (e.g., 86%) detected by the sensor network, the monitoring unit will not produce an alarm condition, and can remind the physician if the physician makes a treatment recommendation under a mistaken belief regarding the "normal" oxygen saturation of this patient. In another example, if a patient who has been taking beta-blockers has a low heart rate, e.g., lower than 40/min, as sensed by the wireless sensor and reported to a physician either remotely or in the physician's office, the system can make that determination and alert the physician that the patient should no longer be prescribed beta-blockers, but should consider other medicine or therapies. As a further example, if a patient is taking an antibiotic, the appropriate dosage of the antibiotic can depend on the weight of the patient such that the patient's kidney function and liver function are not compromised. If the patient's weight has been mistaken when a prescription is given by the physician, the dosage can be incorrect as well, which can lead to ineffective treatment or undesired side effects. In this scenario, the system can validate the dosage prescribed by the physician based on a weight sensor worn by the patient, or by the patient's EMR information stored on a physician computer or downloaded from a server, and alert the physician if the dosage prescribed is not within a predetermined range appropriate for such a patient. As a further example, if a patient visiting a healthcare provider complains about a fever and chest pains, the physician can check the patient's past medical records, which can be stored in the wireless sensors worn by the patient, including the patient's X-ray test result, and determine that the patient is suffering from a pneumonia. If the patient also has a history of alcohol (or other substance) dependence or abuse as indicated by the patient's past medical history, an antibiotic can be prescribed for the patient with an appropriate dosage based on this information as well as the patient's weight and other relevant information, or another therapy can be prescribed for the patient. The prescription can be entered into the monitoring unit of the system or a computer in the physician's office that is wirelessly coupled to the monitoring unit for sending and receiving information. Further, the system can further notify a pharmacy of the entered prescription, and direct the patient to fill the prescription at such a pharmacy. The physiological conditions of a patient of interest, including the effects of a prescribed therapy (including drug treatment, surgical procedures, etc.) on a patient can also be monitored by the patient or the physician by wireless sensors monitoring the vital signs relevant to the prescribed therapy, either in real time (e.g., the data acquired by the sensors can be transmitted in real time or intermittently to a monitoring device accessible by the physician (intermittent transmission refers to transmission of acquired data at a lower interval than the data acquisition or sampling rate by the sensor)), or at each visit to the physician's office by the patient.

The present invention is not to be limited in scope by the specific embodiments described herein. Various modifications of the invention in addition to those described herein will become apparent to those skilled in the art from the foregoing description and the accompanying figures.

One having ordinary skill in the art will recognize that the various mechanisms described for the preferred embodiments of the device may be adapted and interchanged between the preferred embodiments, without significantly impacting the structure and operation of the device. Use of the words "preferred embodiment" or "preferably" is not intended to imply that any other embodiment is less preferred or is not encompassed in the scope of the invention. Those skilled in the art will recognize that the present invention has many applications, may be implemented in many manners and, as such is not to be limited by the foregoing embodiments and examples.

Any number of the features of the different embodiments described herein may be combined into one single embodiment, the locations of particular elements can be altered and alternate embodiments having fewer than or more than all of the features herein described are possible. Functionality may also be, in whole or in part, distributed among multiple components, in manners now known or to become known.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention. While there had been shown and described fundamental features of the invention as applied to being exemplary embodiments thereof, it will be understood that omissions and substitutions and changes in the form and details of the disclosed invention may be made by those skilled in the art without departing from the spirit of the invention. Therefore, the appended claims are intended to cover conventionally known, future developed variations and modifications to the components described herein as would be understood by those skilled in the art.

What is claimed is:

1. A method of managing a heart condition for a subject, the heart condition comprising one or more of ventricular arrhythmia, atrial arrhythmia, ventricular fibrillation, ventricular tachycardia, atrial fibrillation, and bradycardia, the method comprising:
    (a) detecting intrathoracic electrogram signals of the subject over a first defined period of time by at least one implantable cardiac device having a sensor component implanted in the heart of the subject;
    (b) determining whether the subject is experiencing a heart condition based on the electrogram signals;
    (c) detecting ECG signals of the subject over the first defined period of time by at least one surface sensor attached to the skin of a subject,
    (d) determining whether the subject is experiencing the heart condition based on the ECG signals;
    (e) based upon the results of each of steps (b) and (d), determining whether to provide an electrical stimulation to influence an electrical system of the heart of the subject in order to address the heart condition; and
    (f) performing, by the implantable cardiac device, the electrical stimulation if the determination result in step (e) is positive;
    (g) wirelessly sending, by the at least one implantable cardiac device, selected information relating to at least one of the electrogram signals in step (a), the determination result in step (b) and the determination result in step (e) to the at least one surface sensor: and
    (h) wirelessly sending, by the at least one surface sensor, the information received from the at least one implantable cardiac device, as well as selected information relating to at least one of the ECG signals in step (c) and the determination result in step (d), to an external computing device for storage or further analysis.

2. The method of claim 1, wherein the at least one implantable cardiac device is an implantable cardioverter defibrillator or a pacemaker.

3. The method of claim 1, wherein the determining in step (e) further comprises: when the result of step (b) is negative, determining not to perform the electrical stimulation.

4. The method of claim 1, wherein the determining in step (e) further comprises: when the results of steps (b) and (d) are both positive, determining to perform the electrical stimulation.

5. The method of claim 1, wherein the determining in step (e) further comprises: when the result of step (b) is positive and the result of (d) is negative:
    repeating steps (a)-(d) for a predetermined number of times; and
    (j) determining whether to perform the electrical stimulation based on the combination of determination result of each of the repetitions of steps (a)-(d).

6. The method of claim 1, further comprising:
    sending, by the external computing device, an alert to a medical personnel based on the information received by the computing device.

7. The method of claim 1, wherein the determination in each of steps (b), (d), and (e) is performed by a computing device wirelessly linked to each of the at least one surface sensor and the at least one implantable cardiac device based on the ECG signals and electrogram signals received by the computing device from the at least one surface sensor and the at least one implantable cardiac device.

* * * * *